(12) United States Patent
Zhang et al.

(10) Patent No.: US 8,853,485 B2
(45) Date of Patent: Oct. 7, 2014

(54) METHOD FOR PREPARING POLYMER GRADE LOW-CARBON OLEFIN THROUGH SEPARATION OF METHANOL PYROLYSIS GAS

(75) Inventors: Huiling Zhang, Daqing (CN); Longwu Cheng, Daqing (CN); Zhiyuan Song, Daqing (CN); Xiaojian Min, Beijing (CN)

(73) Assignees: China MTO Limited, Hong Kong (CN); Daqing Petrochemical Engineering Co., Ltd., Daqing, Heilongjiang (CN)

( * ) Notice: Subject to any disclaimer, the term of this patent is extended or adjusted under 35 U.S.C. 154(b) by 1092 days.

(21) Appl. No.: 12/294,062

(22) PCT Filed: Jul. 27, 2007

(86) PCT No.: PCT/CN2007/002279
§ 371 (c)(1),
(2), (4) Date: Sep. 23, 2008

(87) PCT Pub. No.: WO2009/015507
PCT Pub. Date: Feb. 5, 2009

(65) Prior Publication Data
US 2010/0234659 A1    Sep. 16, 2010

(51) Int. Cl.
*C07C 7/11*    (2006.01)
*C07C 1/20*    (2006.01)

(52) U.S. Cl.
CPC .... *C07C 7/11* (2013.01); *C07C 1/20* (2013.01)
USPC .......... 585/809; 585/802; 585/833; 585/853; 585/854; 585/864; 585/867

(58) Field of Classification Search
USPC ......... 585/638, 639, 640, 802, 809, 833, 853, 585/854, 864, 867; 62/17, 625, 638, 938
See application file for complete search history.

(56) References Cited

U.S. PATENT DOCUMENTS

| | | | | |
|---|---|---|---|---|
| 4,410,751 A * | 10/1983 | Shin et al. | | 585/640 |
| 4,499,327 A * | 2/1985 | Kaiser | | 585/640 |
| 5,019,143 A * | 5/1991 | Mehra | | 62/625 |
| 5,546,764 A * | 8/1996 | Mehra | | 62/625 |
| 2002/0007101 A1* | 1/2002 | Senetar et al. | | 585/809 |
| 2004/0211703 A1* | 10/2004 | Duhon et al. | | 208/106 |

FOREIGN PATENT DOCUMENTS

| | | |
|---|---|---|
| CN | 1176244 A | 3/1998 |
| CN | 1847203 A | 10/2006 |
| EP | 0 825 245 A2 * | 2/1998 ............. C10G 70/00 |

OTHER PUBLICATIONS

Sundaram, et al., "Ethylene" in Kirk-Othmer Encyclopedia of Chemical Technology, John Wiley & Sons, 2001, available on-line Apr. 16, 2001.*

* cited by examiner

*Primary Examiner* — In Suk Bullock
*Assistant Examiner* — Bradley Etherton
(74) *Attorney, Agent, or Firm* — Burns & Levinson LLP; Jacob N. Erlich; Shahid Hasan (57) ABSTRACT

The present invention provides a method for preparing the polymer grade low-carbon olefin through separation of the methanol pyrolysis gas, including steps of the compression, impurity removal, and absorption and separation. In the absorption and separation step, the pyrolysis gas is sent to the front-end ethylene removing column, and then is, with the C4 absorbent, further absorbed and separated to produce polymer grade ethylene products, polymer grade propylene products, and C4 and C5 products. The moderate-temperature and moderate-pressure separation without a cold box according to the present invention provides safer production process, less investment in the equipment, as well as easier separation and lower energy consumption as a result of the front-end ethylene removing and C4 absorption and separation process.

16 Claims, 4 Drawing Sheets

METHOD FOR PREPARING POLYMER GRADE LOW-CARBON OLEFIN THROUGH SEPARATION OF METHANOL PYROLYSIS GAS

FIELD OF INVENTION

The present invention belongs to light hydrocarbon refining technology, relating to a method for obtaining polymer grade low-carbon olefin through the separation of methanol pyrolysis gas.

BACKGROUND

As the important basic petrochemical raw materials, ethylene and propylene are of important symbolic significance of a country's economic development level. At present, the world's industrial production equipment of ethylene and propylene mainly adopts the steam pyrolysis of the hydrocarbons such as the naphtha and light diesel oil. In such way, the resulted pyrolysis gas is of the mixture which contains the hydrogen, methane, ethane, ethylene, propane, propylene, mixed C4 and C5, and pyrolysis gasoline, etc. and needs to be further separated and refined to produce the qualified chemicals such as the ethylene and propylene.

So far there has been no industrialized device running for preparing the polymer grade low-carbon olefin through the separation of methanol pyrolysis gas at home and abroad. The similar process is the deep cooling separation technology of the steam pyrolysis gas of the naphtha, etc. After multistage compression, in general a 5-stage compression, the pyrolysis gas is up to about 3.7 MPa and then enters the rectification separation system. According to the rectification separation sequence of the hydrocarbons, the rectification separation process is divided into such typical ethylene separation processes as sequential separation process (Lummus/Technip/KBR), front-end deethanizing process (Linde), and front-end depropanizing process (S&W). For the sequential separation process, the latest progress of the Lummus's ethylene separation technology includes the improvement of the compression refrigeration system (3-stage compression medium-pressure pyrolysis and binary/ternary refrigeration system), catalytic rectification hydrogenation (C3 selective hydrogenation), and olefins conversion in which the propylene is produced through the reaction of 2-butene with ethylene. The Technip sequential separation process adopts the 5-stage compression, dual demethanizing columns, and back-end C2 and C3 hydrogenation, and its latest gradual separation technology uses the pinch technology with the minimum energy consumption for the fuzzy separation, and the feedforward control system which is easy to be operated. The KBR separation process adopts the 5-stage compression, 4-stage outlet alkaline scrubbing, front-end high-pressure demethanizing column, back-end C2 and C3 hydrogenation. The front-end deethanizing process adopts the front-end C2 hydrogenation and is applicable for the gas containing a large number of C3+, represented by the Linde process; it is divided into the high-pressure process (3.3 MPa) and low-pressure process (1.18 MPa) depending on the operating pressure of the demethanizing column. For the front-end depropanizing process, after a 3-stage compression of the pyrolysis gas, the fractions lighter than C3 and heavier than C4 are separated, and the acetylene removal is available with the front-end hydrogenation, this process is applicable for the gas containing a large number of C4+. The S&W's latest technical advances include the viscosity control technology of the quenching oil and the HRS cold box patent technology.

The Chinese patent CN1157280A disclosed an energy-saving method for the separation of light hydrocarbon, improving the twin-column front-end deethanizing separation process. This patent provides energy saving through the improved feeding heat exchange mode in the demethanizing column.

The high price of the crude oil at the international market results in the shortage of the naphtha resource. The Methanol to Olefins (hereinafter referred to as MTO) process in which methanol is used as the raw material and then directly transformed into mixed low-carbon olefin through catalytic reaction has been in rapid development in recent years. The MTO's main products include the ethylene and the propylene at a ratio of 0.8 to 1.5 which increases with the increased reaction intensity. The composition of the MTO pyrolysis gas is significantly different from that of the pyrolysis gas of the naphtha etc., mainly embodied in the propylene and propane contained in the MTO pyrolysis gas significantly higher than those in the naphtha pyrolysis gas. If the conventional front-end deethanizing separation process is used for separating the MTO pyrolysis gas, high content of the propylene and propane in the MTO pyrolysis gas will result in the increased power consumption in the 5-stage compression. In addition, such conventional process provides high pressure after the 5-stage compression, and in order to avoid the autoclave in the deethanizing column from overhigh temperature which will lead to the diolefine polymerization, the high- and low-pressure dual columns are generally used for deethanizing. This process is long and complicated, resulting in increased investment. Furthermore, such conventional process, as disclosed in CN1157280A, in general adopts the low-pressure demethanizing technology requiring low temperature of the cold box at the location of the front-end dehydrogenation, which is applicable for the naphtha pyrolysis gas. In the MTO pyrolysis gas, however, the gas impurities contained such as the nitrogen oxides (NOX) and oxygen will lead to the accumulation of the dangerous explosives at the location of the cold box and thus increase insecurity factors of the system.

SUMMARY OF INVENTION

In view of no industrialized devices for preparing the polymer grade low-carbon olefin through separation of the methanol pyrolysis gas running at present at home and abroad, the present invention aims to provide a method for preparing low-carbon olefin products such as the polymer grade ethylene and polymer grade propylene through separation of methanol pyrolysis gas.

Based on the composition characteristics such as high ethylene proportion, high propylene proportion, and nearly equal proportion between ethylene and propylene etc., the present invention provides a new gas refining separation method, which adopts the processes such as the purification of the raw gas, the single-column or multiple-column absorption with the C4 absorbent, and the moderate-temperature (higher than −91° C.) and moderate-pressure (1.1~2.5 MPaG) separation without a cold box, to separate the low-carbon olefin contained in the methanol pyrolysis gas, and finally produce the polymer grade ethylene and polymer grade propylene products, etc.

The present invention provides a method for preparing the polymer grade low-carbon olefin through separation of the methanol pyrolysis gas, comprising the steps of:
  (1) Compression: the methanol pyrolysis gas being sent into the compression system for multistage compression;

(2) Impurity removal: the methanol pyrolysis gas compressed in step (1) being impurity-removed in the impurity removal system to obtain the refined pyrolysis gas;

(3) Absorption and separation: the refined pyrolysis gas obtained in step (2) being separated through the absorption and separation system, during which said gas being firstly sent into the front-end ethylene removing column, and then further absorbed and separated to produce the polymer grade ethylene products, polymer grade propylene products, and C4 and C5 products.

In said step (1), the methanol pyrolysis gas can be up to 1.1-2.5 MPaG through the three- to four-stage compression.

In said step (2), the impurity removal system used includes one or combination of an alkaline scrubbing column, an acetylene remover, a deaerator and a drying column. In the refined pyrolysis gas processed in said step (2), the $CO_2$ concentration is less than 1 ppm, and/or the total content of the alkyne is less than 5 ppm.

The refined pyrolysis gas obtained in said step (2) provides the polymer grade ethylene products and the C4 fraction by being processed in turn through the front-end ethylene removing column, ethylene absorption column, demethanizing column and ethylene fractionating column, and/or provides the polymer grade propylene and C5 products by being processed in turn through the front-end ethylene removing column, deethanizing column, depropanizing column and propylene rectification tower.

The refined pyrolysis gas obtained in said step (2) is firstly sent into the front-end ethylene removing column, in the upper portion of which the components contained enter the ethylene absorption column; then the components in the upper portion of the ethylene absorption column enter the ethylene recovery column, in the upper portion of which the components contained enter the PSA unit to recover the hydrogen contained; the components at the lower portion of the ethylene absorption column is further demethanized through the demethanizing column and then goes into the ethylene fractionating column, in the upper portion of which the polymer grade ethylene products are obtained. The C4 fraction is obtained in the lower portion of the ethylene fractionating column, and includes three parts: a part used as the C4 products, a part returning to the bottom of the ethylene absorption column as the heat feeds, and other part entering the upper portion of the ethylene recovery column as the absorbents.

In said step (3), the components from the lower portion of the ethylene recovery column and the refined pyrolysis gas obtained in said step (2) are sent to the front-end ethylene removing column.

In said step (3), the components in the upper portion of the front-end ethylene removing column are firstly cooled, and then enter the ethylene absorption column, where the ethylene component contained is absorbed by the C4 fraction.

In said step (3), the components in the upper portion of the ethylene absorption column enter the ethylene recovery column, where the ethylene component contained is further absorbed by the C4 fraction cooled to −60° C. to −85° C. The above-mentioned C4 fraction used for absorbing the ethylene component in the ethylene recovery column is of such a part that is in the C4 fraction obtained in the lower portion of the ethylene fractionating column and after being cooled, enters the upper portion of the ethylene recovery column.

In said step (3), the components in the lower portion of the front-end ethylene removing column are sent to the deethanizing column, in the lower portion of which the components contained enter the depropanizing column; the components in the upper portion of the depropanizing column are, through the propylene rectification tower, further separated to obtain the polymer grade propylene products. The components in the lower portion of the depropanizing column are sent into the debutanizing column, from the lower portion of which the C5 products are obtained.

In said step (3), after the components in the lower portion of the front-end ethylene removing column enter the deethanizing column, the materials in the upper portion of the deethanizing column are recovered and cooled to obtain the ethane products.

In said step (3), the propane products are also obtained from the lower portion of the propylene rectification tower.

In said step (3), after the components in the lower portion of the depropanizing column enter the debutanizing column, the C4 fraction in the upper portion of the debutanizing column are cooled and then sent into the ethylene absorption column as the absorbent.

In the polymer grade ethylene products obtained with the method for preparing polymer grade low-carbon olefin through separation of methanol pyrolysis gas according to the present invention, the volume content of the ethylene is greater than 99.95%, and/or that of the propylene in the polymer grade propylene products is more than 99.5%.

The present invention adopts the front-end ethylene removing process, in which the C4 solvent is used as the absorbent to absorb and separate the ethylene component and thus separate the polymer grade ethylene and polymer grade propylene at a low pressure, with gentle and safe operating conditions. The moderate-temperature (higher than −91° C.) separation without a cold box in the present invention provided safer production process, thus avoiding the accumulation of hazardous impurities. Meanwhile, The moderate-pressure (1.1~2.5 MPaG) separation provides saved investment in equipment and decreases the number of the compressor's sections. Moreover, as a result of the front-end ethylene removing process, in which the ultimate refining of the ethylene is the separation from the C4 absorbent, the separation is easier with lower energy consumption.

The other features and advantages of the present invention are further described in following detailed description of the present invention. Those skilled in the art will readily understand the present invention through reading the description, claims and attached drawings of the present invention, or through implementing the present invention according to the description, claims and attached drawings. The parts not described in detail herein, such as the processes of compression, alkaline scrubbing, deaerating, drying and fractionation of the raw gas, all are the well-known technologies in this technical field.

The method of the present invention is described as follows with reference to the attached drawings and the preferred embodiments, but all the specific parameters and process conditions given in these figures and embodiments are only for demonstrative description of the present invention, and will not constitute any restriction to the present invention.

DESCRIPTION OF DRAWINGS

The attached drawings of this application provide further assistance for understanding the present invention, and constitute a part of the description of the present invention, in which.

DESCRIPTION OF THE PREFERRED EMBODIMENTS

Figure 1:
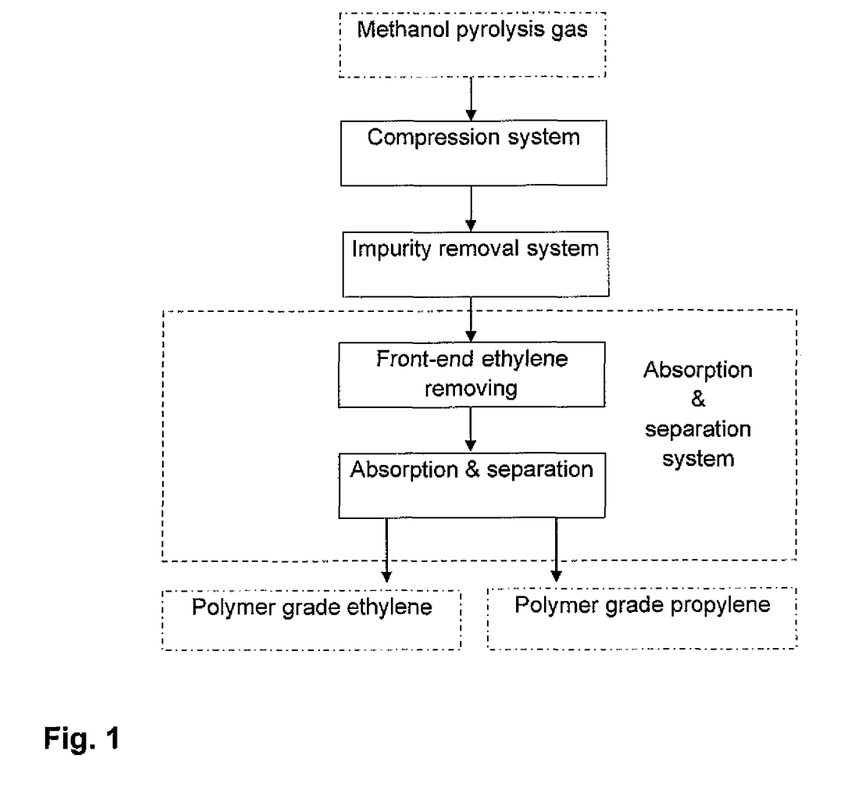
FIG. 1 shows the flow diagram of the present invention.

The present invention is a novel technology developed for separation of methanol pyrolysis gas. As shown in FIG. 1, its technical solution is such that the methanol pyrolysis gas is used as the raw material to extract the polymer grade ethylene and polymer grade propylene from the pyrolysis gas through the compression, impurity removal, and absorption and separation systems, etc.

The specific process steps are as follows:

(1) Compression step: the methanol pyrolysis gas is sent into the compression system for the 3- to 4-stage compression up to 1.1~2.5 MPaG and then enters the impurity removal system. This compression system may adopt the multistage compression system which is well-known and used commonly in the art, it is enough for the final pressure up to 1.1~2.5 MPaG, without need for higher pressure.

Figure 2:
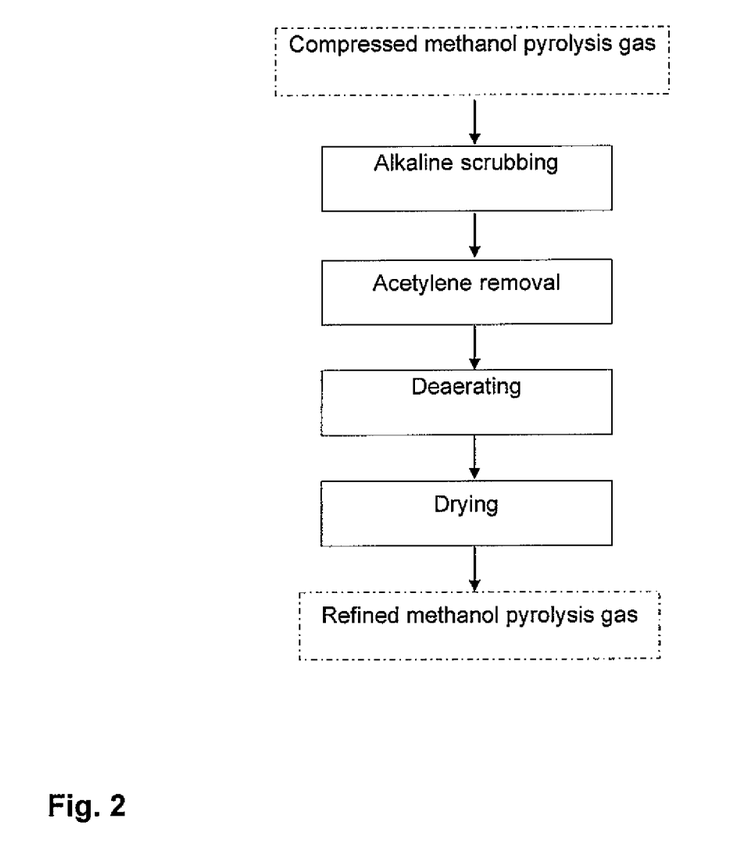
FIG. 2 shows the flow diagram of the impurity removal system according to an embodiment of the present invention.

(2) Impurity removal step: the compressed methanol pyrolysis gas enters the impurity removal system for impurity removal. Firstly, the compressed pyrolysis gas may enter the alkaline scrubbing column to remove the acidic substances such as $CO_2$ using the NaOH water solution, or depending on the conditions of the raw materials, additionally using the amine washing process. Then, the pyrolysis gas enters in turn the acetylene remover, deaerator and drying column to remove impurities such as the alkyne, oxygen and water. Finally, the refined pyrolysis gas goes into the absorption and separation system (FIG. 2).

Figure 3:
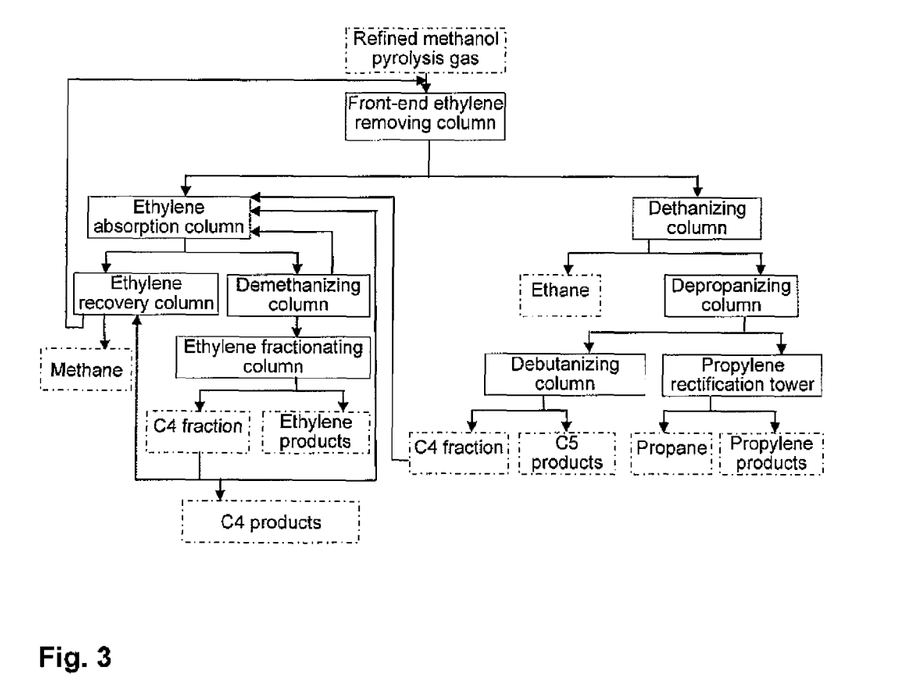
FIG. 3 shows the flow diagram of the absorption and separation system according to an embodiment of the present invention.

(3) Absorption and separation step: the refined pyrolysis gas then enters the absorption and separation system for separation. The refined methanol pyrolysis gas firstly goes into the front-end ethylene removing column to be separated into the ethylene and light components in the upper portion of the column as well as the materials in the lower portion of the column, which respectively enter the ethylene absorption column and the deethanizing column. After the dry gas in the upper portion of the ethylene absorption column enters the ethylene recovery column for further absorption of the ethylene component contained, the methane and hydrogen etc., in the upper portion of the ethylene recovery column enter the PSA unit to recover the hydrogen contained, and the materials in the lower portion of the ethylene recovery column return into the front-end ethylene removing column to be fed. After entering the demethanizing column for further being demethanized, the materials in the lower portion of the ethylene absorption column are separated into the polymer grade ethylene products through the ethylene fractionating column. In the C4 fraction in the lower portion of the ethylene fractionating column, a part returns to the lower portion of the ethylene absorption column as the heat feeds, a part enters the upper portion of the ethylene recovery column, and the residual part is used as the C4 products. The materials in the upper portion of the dethanizing column are used as the ethane products; the fraction in the lower portion of the dethanizing column enters the depropanizing column. The components in the upper portion of the depropanizing column enter the propylene rectification tower for further separation to obtain the polymer grade propylene products, and in the lower portion of the propylene rectification tower, the propylene by-products are obtained by separating. The fraction in the lower portion of the depropanizing column goes into the debutanizing column. The C4 fraction in the upper portion of the debutanizing column enters the ethylene absorption column as the absorbent, and the C5 products are separated from the lower portion of the column (FIG. 3).

Figure 4:
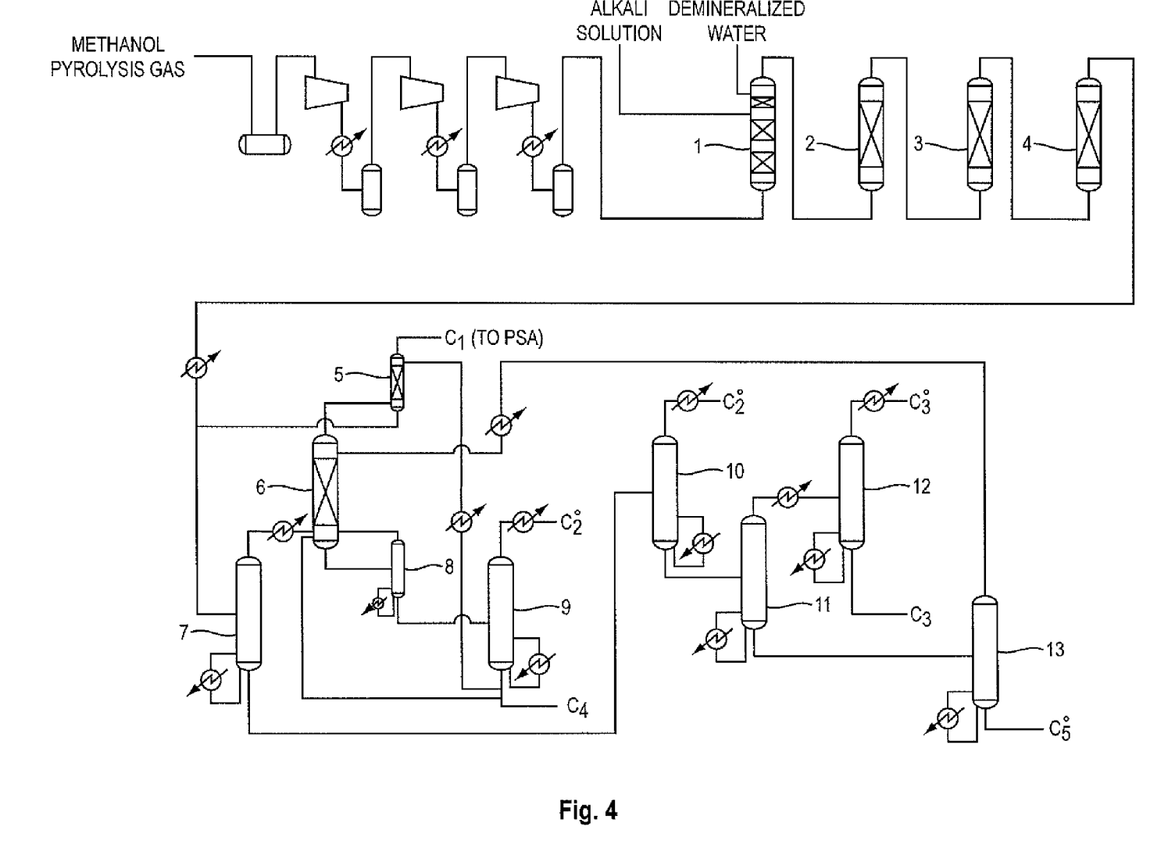
FIG. 4 shows the sketch of the preparation process according to an embodiment of the present invention.

The FIG. 4 graphically shows a view of the preparation process according to an embodiment of the present invention. The compression system in FIG. 4 is of a 3-stage compression. It compresses the methanol pyrolysis gas to 1.1 to 2.5 MPaG which then is sent to the impurity removal system for purification through the alkaline scrubbing column 1, acetylene remover 2, deaerator 3 and drying column 4. In the refined pyrolysis gas processed, the $CO_2$ concentration is less than 1 ppm and/or the total content of the alkyne is less than 5 ppm. Then, the refined pyrolysis gas is sent into the absorption and separation system for separation. The refined methanol pyrolysis gas, together with the C1, C2 and C4 components from the lower portion of the ethylene recovery column 5, enters the front-end ethylene removing column 7. The ethylene and light components are available in the upper portion of the column, and the materials in the lower portion of the column enter the deethanizing column 10. The light components at the upper portion of the front-end ethylene removing column 7 are cooled and then enter the ethylene absorption column 6 where the ethylene component contained is absorbed by the C4 fraction. The dry gas in the upper portion of the column 6 enters the ethylene recovery column 5 for further absorption of the ethylene component contained with the C4 fraction which is cooled to −60° C. to −85° C. The methane (C1) and hydrogen etc., in the upper portion of the column 5 enter the PSA unit for recovery of the hydrogen; the materials in the lower portion of the column 5 return to the column 7 to be fed. The liquid phase in the lower portion of the ethylene absorption column 6 enters the demethanizing column 8 for further demethanization, and then produce the polymer grade ethylene products (C2=) through the ethylene fractionating column 9. In the C4 fraction in the lower portion of the ethylene fractionating column 9, a part returns to the bottom of the ethylene absorption column 6 as the heat feeds, a part is cooled and then enters the upper portion of the ethylene recovery column 5, and the residual part is used as the C4 products. The materials in the upper portion of the deethanizing column 10 are used as the ethane products (C20) after recovery and being cooled; the fraction in the lower portion of the deethanizing column 10 enters the depropanizing column 11, in the upper portion of which the C3 component contained enters the propylene rectification tower 12 for further separation to obtain the polymer grade propylene products (C3=). In the lower portion of the propylene rectification tower 12, the propylene by-products (C3) are separated. The fraction in the lower portion of the depropanizing column 11 goes into the debutanizing column 13, in the upper portion of which the C4 fraction contained is cooled and then enter the upper portion of the ethylene absorption column 6 as the absorbent, and the C5 products (C5+) are separated from the lower portion of the column.

Main operating conditions of processes:
Compression system
Outlet pressure of compressor: 1.1 to 2.5 MpaG.
Impurity removal system CO₂ concentration after scrubbing with the alkali solution: ≤1 ppm;
Total alkyne content: ≤5 ppm.
Absorption and separation system
Polymer grade ethylene: ethylene content: ≥99.95% (v);
Polymer grade propylene: propylene content: ≥99.5% (v).

EXAMPLE

The methanol pyrolysis gas is subject to the 3- to 4-stage compression up to 1.1-2.5 MPaG and then sent into the impurity removal system. The compressed methanol pyrolysis gas enters the alkaline scrubbing column to remove the acidic substances such as CO2 using the NaOH water solution, or depending on the conditions of the raw materials, additionally using the amine washing process. Then, the pyrolysis gas enters in turn the acetylene remover, deaerator and drying column to remove impurities such as the alkyne, oxygen and water. Finally, the refined pyrolysis gas goes into the absorption and separation system.

The refined pyrolysis gas is cooled with the propylene refrigerant in the pyrolysis gas cooler, and then enters the front-end ethylene removing column, which uses hot water as the reboiler's heat source. For the gas in the upper portion of the front-end ethylene removing column, the −60 to −40° C. ethylene refrigerant is used for cooling. In the upper portion of the column, there are the ethylene and other light components which are sent into the ethylene absorption column of the demethanizing system. In the lower portion of the column, there are the ethane and other heavy components which are pumped into the deethanizing column.

The materials from the upper portion of the front-end ethylene removing column enter the ethylene absorption column which adopts C4 for the backflow. Such backflow C4 comes from the C4 in the upper portion of the debutanizing column and is cooled with the propylene refrigerant. The backflow C4 absorbs the ethylene in the methane tail-gas while a part of C4 is vaporized and mixed into said tail-gas. The methane tail-gas in the upper portion of the column enters the ethylene recovery column, and the materials in the lower portion of the column are pumped into the demethanizing column.

The materials from the upper portion of the ethylene absorption column enter the lower portion of the ethylene recovery column which adopts C4 as the absorbent. The C4 absorbent is from C4 in the lower portion of the ethylene fractionation tower. C4 is cooled by the materials of the demethanizing column's reboiler and the ethylene refrigerant. The methane gas in the upper portion of the column is subjected to the energy recovery through the methane gas heater and then sent into the PSA hydrogen generation system. The bottom materials of the demethanizing column are pumped to the front-end ethylene removing system, and after being mixed with the pyrolysis gas, enter the front-end ethylene removing column.

The materials from the lower portion of the ethylene absorption column enter the demethanizing column which uses the bottom C4 of the ethylene fractionation tower as the reboiler's heat source. The gas in the upper portion of the demethanizing column is cooled with the −80 to −50° C. refrigerant, and the top materials return to the middle part of the ethylene absorption column. In the lower portion of the column, there are the ethylene and C4 components. The polymer grade ethylene is produced in the ethylene fractionating column.

The materials from the lower portion of the front-end ethylene removing column enter the deethanizing column to separate into the ethane, C3 and other heavy components. The remaining component separation sequence and operating conditions are similar to the method of the steam pyrolysis and separation of the hydrocarbons such as the naphtha, and thus not detailed herein. The Table 1 lists the process parameters of one preferred embodiment of the present invention:

TABLE 1

| Process parameter | Value |
| --- | --- |
| Pressure of pyrolysis gas (MPaG) | 1.1 |
| Pressure of front-end ethylene removing column (MPaG) | 0.97 |
| Temperature in the upper portion of front-end ethylene removing column (° C.) | −53 |
| Temperature in the lower portion of front-end ethylene removing column (° C.) | 34 |
| Pressure of ethylene absorption column (MPaG) | 0.89 |
| Temperature in the upper portion of ethylene absorption column (° C.) | −19 |
| Temperature in the lower portion of ethylene absorption column (° C.) | −49 |
| Pressure of ethylene recovery column (MPaG) | 0.75 |
| Temperature in the upper portion of ethylene recovery column (° C.) | −68 |
| Temperature in the lower portion of ethylene recovery column (° C.) | −34 |
| Pressure of demethanizing column (MPaG) | 1.3 |
| Temperature in the upper portion of demethanizing column (° C.) | −65 |
| Temperature in the lower portion of demethanizing column (° C.) | −27 |
| Pressure of ethylene fractionating column (MPaG) | 2.56 |
| Temperature in the upper portion of ethylene fractionating column (° C.) | −18 |
| Temperature in the lower portion of ethylene fractionating column (° C.) | 128 |

According to these process parameters, the ethylene content in the polymer grade ethylene products is up to 99.95%, and the propylene content in the polymer grade propylene products is up to 99.5%.

Table 2 lists the process parameters of another preferred embodiment of the present invention:

TABLE 2

| Process parameter | Value |
| --- | --- |
| Pressure of pyrolysis gas (MPaG) | 2.5 |
| Pressure of front-end ethylene removing column (MPaG) | 2.37 |
| Temperature in the upper portion of front-end ethylene removing column (° C.) | −26 |
| Temperature in the lower portion of front-end ethylene removing column (° C.) | 70 |
| Pressure of ethylene absorption column (MPaG) | 2.29 |
| Temperature in the upper portion of ethylene absorption column (° C.) | −15 |
| Temperature in the lower portion of ethylene absorption column (° C.) | −27 |
| Pressure of ethylene recovery column (MPaG) | 1.95 |
| Temperature in the upper portion of ethylene recovery column (° C.) | −61 |
| Temperature in the lower portion of ethylene recovery column (° C.) | −47 |
| Pressure of demethanizing column (MPaG) | 2.7 |
| Temperature in the upper portion of demethanizing column (° C.) | −74 |
| Temperature in the lower portion of demethanizing column (° C.) | −1 |
| Pressure of ethylene fractionating column (MPaG) | 2.56 |
| Temperature in the upper portion of ethylene fractionating column (° C.) | −18 |
| Temperature in the lower portion of ethylene fractionating column (° C.) | 127 |

According to these process parameters, the ethylene content in the polymer grade ethylene products is up to 99.95%, and the propylene content in the polymer grade propylene products is up to 99.5%.

The invention claimed is:

1. A method for preparing low-carbon olefin products comprising a polymer grade ethylene and/or a polymer grade propylene comprising:
   (1) providing a stream of methanol pyrolysis gas comprising ethylene, propylene, $C_4$ hydrocarbons, and $C_5$ hydrocarbons, wherein the ratio of said ethylene to said propylene in said methanol pyrolysis gas is at least about 0.8 to about 1.5 by volume;
   (2) compressing the methanol pyrolysis gas from step (1) in a compression system for a three- to four-stage compression, to obtain a compressed methanol pyrolysis gas having a pressure of about 1.1 to about 2.5 MPaG;
   (3) removing at least one impurity from the compressed methanol pyrolysis gas from step (2) in an impurity removal system to obtain a refined methanol pyrolysis gas comprising a $CO_2$ concentration of less than 1 ppm and/or a total content of an alkyne less than about 5 ppm by volume;
   (4) cooling said refined methanol pyrolysis gas from step (3) with a propylene refrigerant in a pyrolysis gas cooler to obtain a cooled refined methanol pyrolysis gas;
   (5) passing the cooled refined methanol pyrolysis gas from step (4) into a front-end ethylene removing column comprising an upper portion and a lower portion, wherein said upper portion is maintained at a temperature ranging between about −53° C. and about −26° C., to produce an upper stream comprising ethylene and light components;
   (6) passing the upper stream from the front-end ethylene removing column from step (5) to an ethylene absorption column maintained at a temperature ranging between about −15° C. to about −53° C. where an absorbent comprising $C_4$ hydrocarbons contacts the upper stream from the front-end ethylene removing column to produce a lower liquid stream comprised of ethylene and absorbent and an upper vapor stream comprised of absorbent, ethylene and light gases;
   (7) passing the upper vapor stream from the ethylene absorption column from step (6) into an ethylene recovery column maintained at a temperature ranging between about −68° C. and −34° C. where the absorbent comprising $C_4$ hydrocarbons contacts the upper vapor stream from the ethylene absorption column to produce an upper stream comprised of absorbent and light gases and a lower stream comprised of ethylene and absorbent;
   (8) passing the lower liquid stream from the ethylene recovery column from step (7) to the front-end ethylene removing column;
   (9) passing the lower liquid stream from the ethylene absorption column from step (7) to a demethanizing column maintained at a temperature ranging between about −27° C. to about −65° C. to produce an upper stream and a lower stream;
   (10) passing the lower stream from the demethanizing column in step (9) into an ethylene fractionating column maintained at a temperature ranging from about −18° C. to about 128° C.; and,
   (11) obtaining polymer grade ethylene comprising greater than 99.95% by volume ethylene from the ethylene fractionating column.

2. The method of claim 1, wherein the impurity removal system used in said step (3) is selected from the group consisting of an alkaline scrubbing column, an acetylene remover, a deaerator, and a drying column and a combination thereof.

3. The method of claim 1 wherein said demethanization of said cooled refined methanol pyrolysis gas comprises removal of methane gases, said methane gases are subjected to an energy recovery through a methane gas heater followed by a passage into a PSA hydrogen generation system.

4. The method of claim 1 wherein the demethanized refined methanol pyrolysis gas is pumped into the front-end ethylene removing column, and after being mixed with the methanol pyrolysis gas, enters the front-end ethylene removing column.

5. The method of 1 wherein said front-end ethylene removing column further comprises a lower portion maintained at a temperature ranging between about 34° C. and about 70° C.

6. The method of claim 5, where the components comprising propylene, $C_4$ hydrocarbons, and $C_5$ hydrocarbons are withdrawn from the lower portion of the front-end ethylene removing column and are routed to a deethanizing column from the lower portion of which the components are routed to a depropanizing column comprising an upper and a lower portion and components in the upper portion of the depropanizing column are routed through a propylene rectification tower comprising an upper and a lower portion and are further separated to obtain the polymer grade propylene comprising a volume content of propylene greater than 99.5%.

7. The method of claim 6, wherein the components in the lower portion of the depropanizing column are routed to a debutanizing column comprising an upper and a lower portion from the lower portion of which the $C_5$ hydrocarbons are produced.

8. The method of claim 7, wherein after the components in the lower portion of the depropanizing column enter the debutanizing column, the $C_4$ hydrocarbons produced in the upper portion of the debutanizing column are cooled and sent into the ethylene absorption column as the absorbent.

9. The method of claim 6, wherein after the components in the lower portion of the front-end ethylene removing column enter the deethanizing column, the materials in the upper portion of the deethanizing column are recovered and cooled to obtain the ethane products.

10. The method of claim 6, where in said lower portion of the propylene rectification tower propylene byproducts are separated.

11. The method of claim 1 wherein said separation of said polymer grade ethylene products occurs without the use of a cold box.

12. The method of claim 1 wherein pressure in said front-end ethylene removing column is about 0.97 MPaG.

13. The method of claim 1 wherein pressure in said ethylene absorption column is about 0.89 MPaG.

14. The method of claim 1 wherein pressure of ethylene recovery column is about 0.75 MPaG.

15. The method of claim 1 wherein pressure in said ethylene fractionating column is about 2.56 MPaG.

16. The method of claim 1 wherein each of said ethylene absorption column and said ethylene fractionating column each comprise a lower and an upper portion.

* * * * *